(12) United States Patent
Beckman et al.

(10) Patent No.: US 8,075,482 B2
(45) Date of Patent: Dec. 13, 2011

(54) IRIS VALVE WITH CONTROL RING

(75) Inventors: Andrew T. Beckman, Cincinnati, OH (US); Patrick J. Minnelli, Harrison, OH (US); Anthony T. Nguyen, West Chester, OH (US); Chester O. Baxter, III, West Chester, OH (US); Michele D'Arcangelo, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1067 days.

(21) Appl. No.: 11/677,820

(22) Filed: Feb. 22, 2007

(65) Prior Publication Data

US 2008/0208175 A1  Aug. 28, 2008

(51) Int. Cl.
*A61B 1/32* (2006.01)

(52) U.S. Cl. .......................................................... 600/208

(58) Field of Classification Search ................... 600/206, 600/207, 208, 210, 201, 213, 215
See application file for complete search history.

(56) References Cited

U.S. PATENT DOCUMENTS

| | | | |
|---|---|---|---|
| 3,666,136 A * | 5/1972 | Lopez | 220/288 |
| 5,088,500 A | 2/1992 | Wedel et al. | |
| 5,366,478 A | 11/1994 | Brinkerhoff et al. | |
| 5,526,536 A | 6/1996 | Cartmill | |
| 5,545,179 A | 8/1996 | Williamson, IV | |
| 5,653,705 A | 8/1997 | de la Torre et al. | |
| 5,672,168 A | 9/1997 | de la Torre et al. | |
| 5,741,298 A | 4/1998 | MacLeod | |
| 5,906,577 A | 5/1999 | Beane et al. | |
| 5,925,064 A | 7/1999 | Meyers et al. | |
| 5,947,922 A | 9/1999 | MacLeod | |
| 5,957,913 A | 9/1999 | de la Torre et al. | |
| 6,024,736 A | 2/2000 | de la Torre et al. | |
| 6,142,936 A | 11/2000 | Beane et al. | |
| 6,159,200 A | 12/2000 | Verdura et al. | |
| 6,165,184 A | 12/2000 | Verdura et al. | |
| 6,319,246 B1 | 11/2001 | de la Torre et al. | |
| 6,440,063 B1 | 8/2002 | Beane et al. | |
| 6,485,425 B2 | 11/2002 | Seward et al. | |
| 6,735,470 B2 | 5/2004 | Henley et al. | |
| 6,746,402 B2 | 6/2004 | Ustuner | |
| 6,840,951 B2 | 1/2005 | de la Torre et al. | |
| 7,008,377 B2 | 3/2006 | Beane et al. | |

(Continued)

FOREIGN PATENT DOCUMENTS

CN          2299595          12/1998

OTHER PUBLICATIONS

PCT International Search Report dated Jul. 2, 2008 for corresponding patent application, Patent Application No. PCT/US2008/054278.

*Primary Examiner* — Eduardo C Robert
*Assistant Examiner* — Summer L Kostelnik (57) ABSTRACT

A laparoscopic surgical access device comprises a first frame and a second frame having relative axial positions. A flexible and resilient iris valve is connected to the first and second frames and has a closed position and an opened position based on the relative angular position of the first and second frames. A lock is connected to the first and second frames, the lock being selectively operative to prevent relative rotational movement in a first rotational direction. One embodiment uses a ratchet and pawl mechanism operable with a control ring. Another embodiment uses a ratchet and pawl mechanism operable with a button. Yet another embodiment uses a wedge track and ball mechanism.

17 Claims, 11 Drawing Sheets

U.S. PATENT DOCUMENTS

| | | |
|---|---|---|
| 2004/0054353 A1 | 3/2004 | Taylor et al. |
| 2004/0231167 A1 | 11/2004 | Miklos |
| 2004/0267133 A1 | 12/2004 | Podany |
| 2005/0222582 A1 | 10/2005 | Wenchell |
| 2005/0234304 A1* | 10/2005 | Dewey et al. ............ 600/210 |
| 2005/0251093 A1 | 11/2005 | Abou-Kansoul |
| 2006/0247500 A1 | 11/2006 | Voegele et al. |
| 2008/0146884 A1* | 6/2008 | Beckman et al. ............ 600/208 |

* cited by examiner

IRIS VALVE WITH CONTROL RING

BACKGROUND

The present invention relates in general to surgical devices and procedures, and more particularly to access devices.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Access devices are often used to facilitate surgical manipulation of internal tissue while maintaining pneumoperitoneum. For example, trocars are often used to provide a port through which endoscopic surgical instruments are passed. Trocars generally have a sealing valve that prevent the insufflatory fluid from escaping while an instrument is positioned in the trocar. As a further example, hand access devices are also used during endoscopic surgery, sometimes referred to as hand assisted laparoscopic surgery ("HALS"). A HALS access device will typically seal around a surgeon's hand or arm to prevent the insufflatory fluid from escaping while allowing the surgeon to manipulate tissue within the patient's body. Iris valves are sometimes used to provide a seal in access devices.

While access devices and iris seals are known, no one has previously made or used an access device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

DETAILED DESCRIPTION

Figure 1:
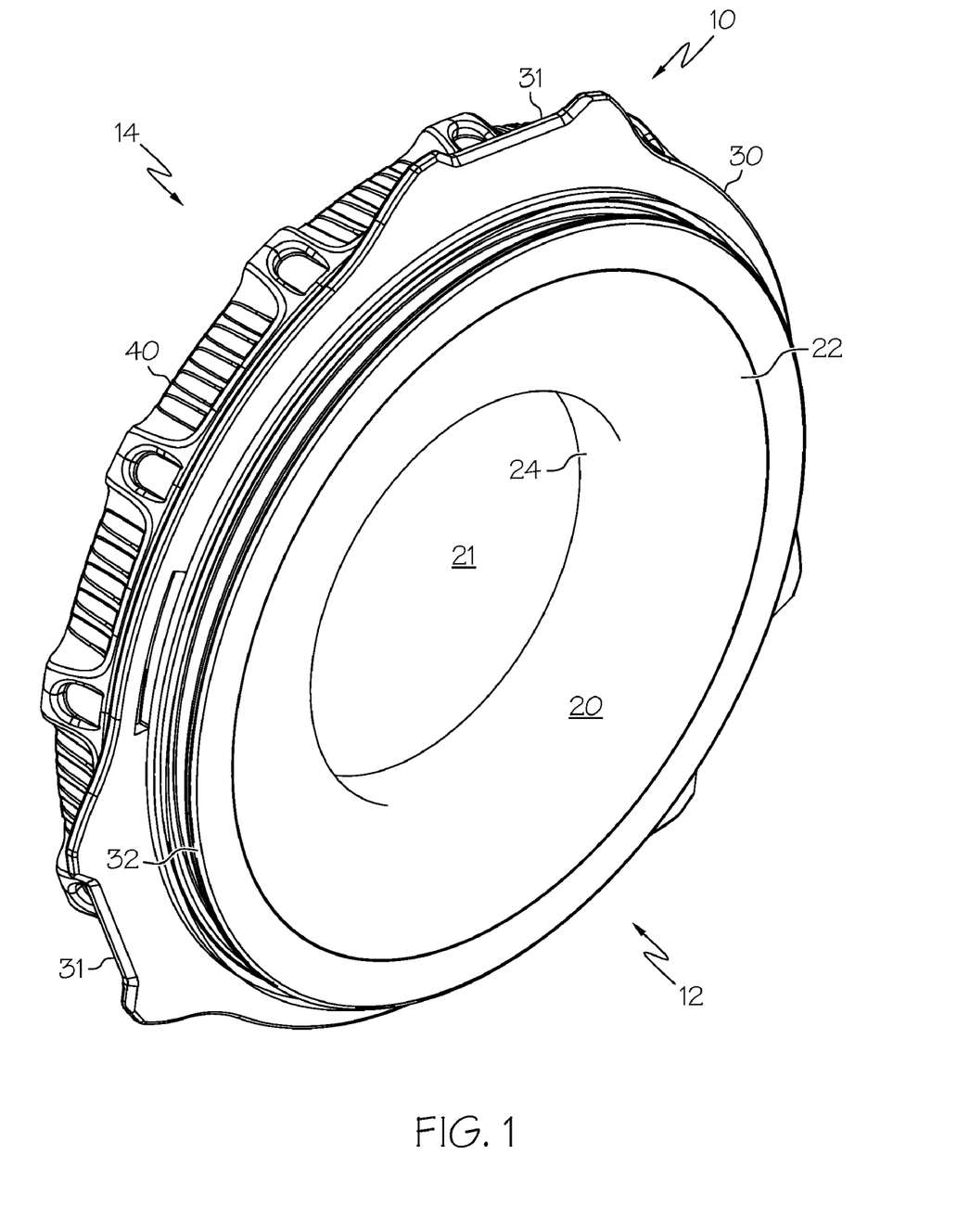
FIG. 1 depicts a perspective view of an access device with an iris valve in an opened position.
Figure 2:
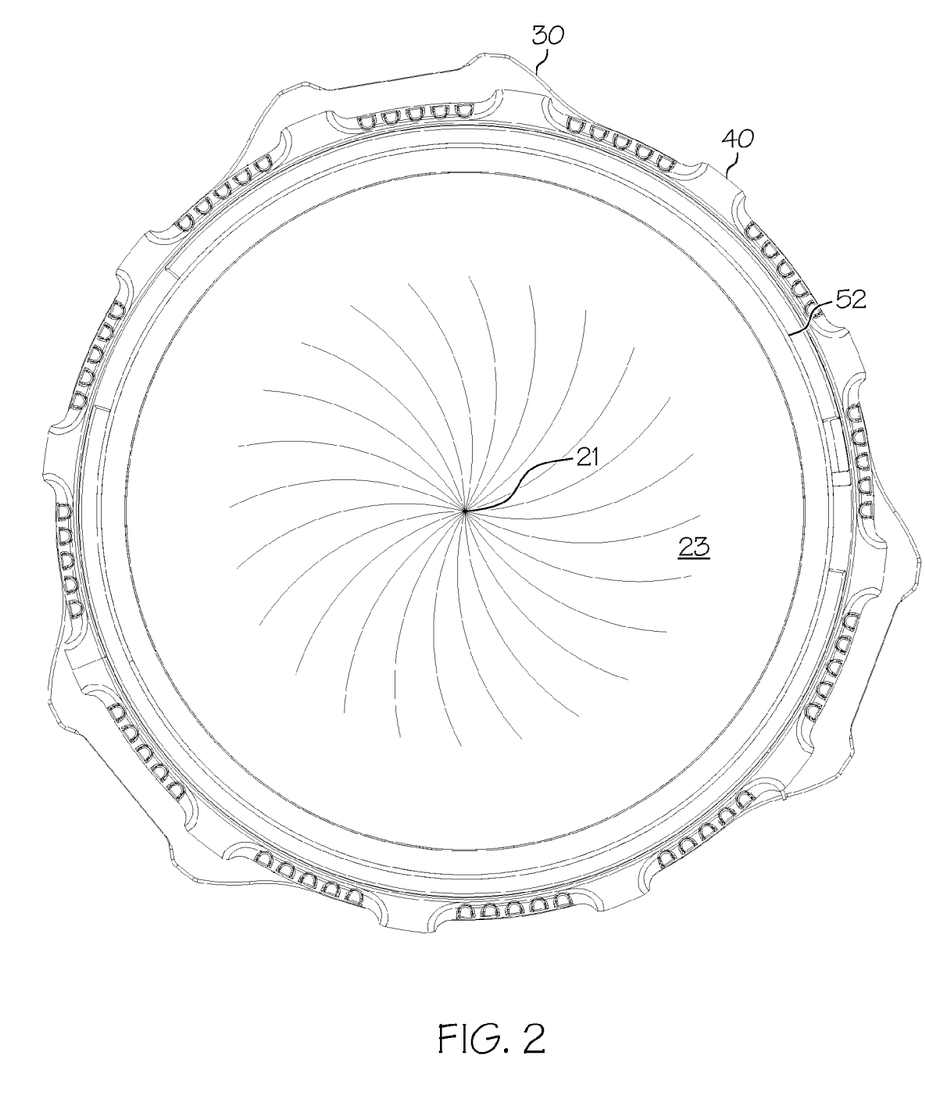
FIG. 2 depicts a top plan view of an access device with the iris valve in a closed position.
Figure 3:
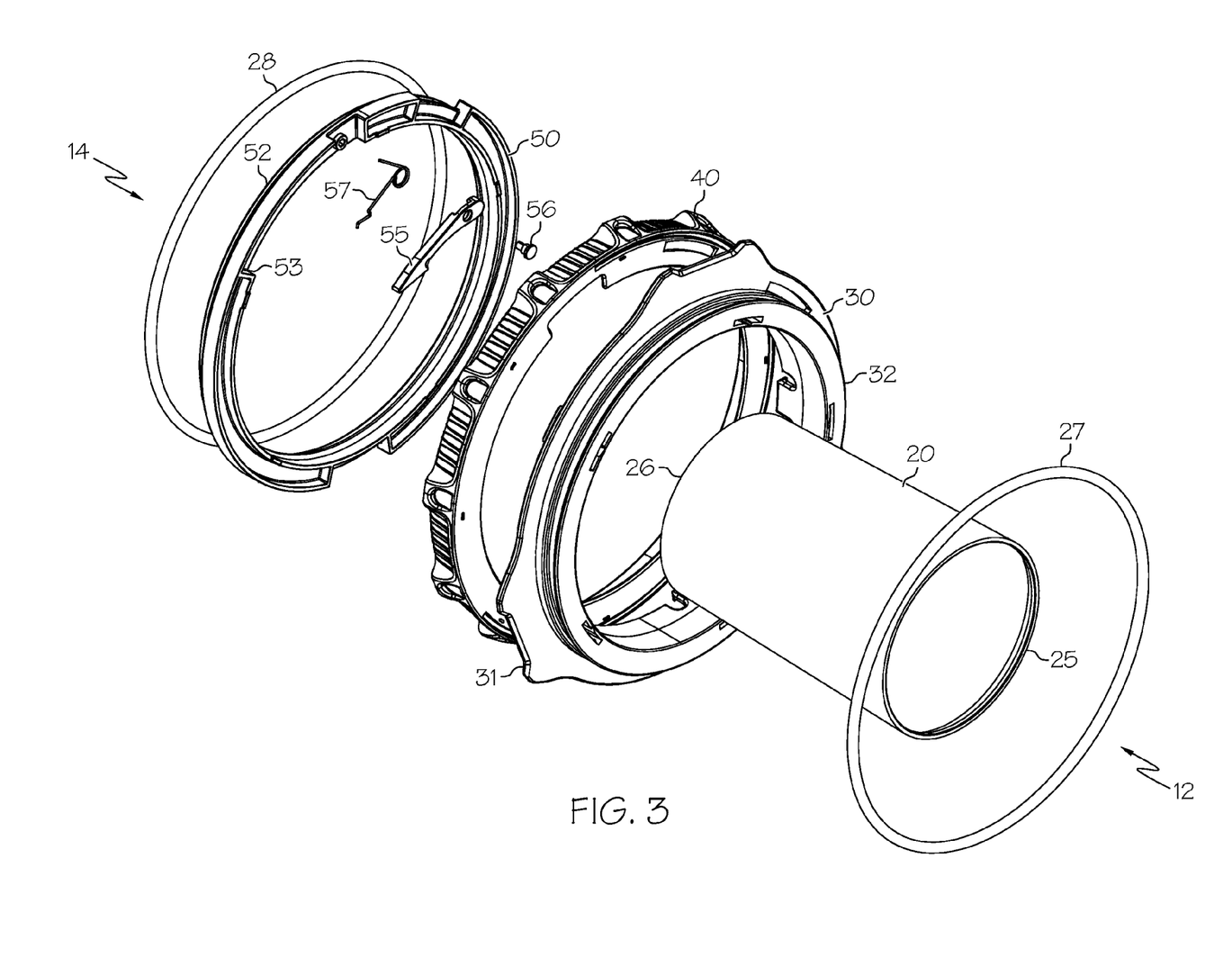
FIG. 3 depicts an exploded view of an access device.
Figure 4:
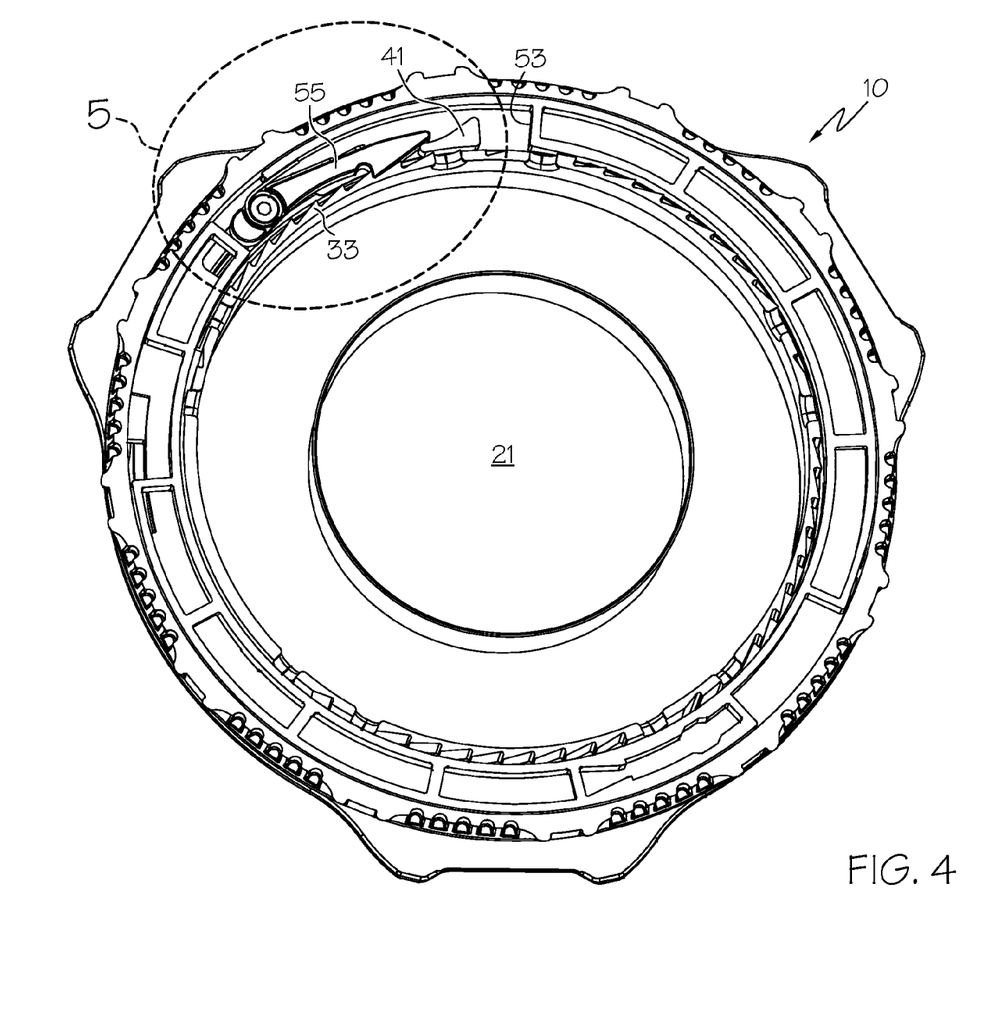
FIG. 4 depicts cross-sectional view of an access device.

FIGS. 1-3 illustrate an access device (10) with an iris valve (20) adapted for HALS procedures. The access device has a distal face (12) adapted to face the patient and a proximal face (14) adapted to face away from the patient. The access device (10) includes an adjustable iris valve (20) having an opened position and a closed position. As shown in FIG. 1, the iris valve (20) is in a fully opened position resulting in a passage (21) adapted to receive a surgeon's hand and arm or surgical instruments. As shown in FIG. 2, the iris valve is in a closed position where the passage (21) is closed. The passage (21) is adjustable to a variety of sizes between the opened and closed positions to seal against the surgeon's arm during a HALS procedure and maintain pneumoperitoneum.

The access device (10) may also include a wound protector (not shown). As one with ordinary skill in the art will recognize, wound protectors are often placed in an abdominal incision to prevent infection, facilitate wound retraction, and seal against the abdominal wall to maintain pneumoperitoneum. Suitable wound protectors may be rigid or flexible and may be fixed or variable length. In this embodiment the tabs (31) are provided to detachably connect the access device (10) to a wound protector; however, it could also be permanently attached.

In this embodiment the iris valve (20) comprises a flexible and resilient diaphragm member. In the assembled access device (10) as shown in FIGS. 1 and 2, the iris valve (20) includes a radial extending distal flange portion (22), a radial extending proximal flange portion (23), and an transition portion (24) defining the passage (21). As shown in FIG. 3, prior to assembly the iris valve (20) is a generally tubular shape made from an resilient material such as polyisoprene, silicone, or polyurethane with a thickness less than about 0.02 inches, and preferably between 0.009 to 0.02 inches. The flange portions (22, 23) are formed by radially stretching the tube such that the distal and proximal ends (25, 26) attach to lips (32, 52) on the frame members (30, 50), respectively. O-rings (27, 28) also engage the ends (25, 26) near the lips and facilitate the connections and seals. Optionally, the o-rings (27, 28) could be incorporated into the iris valve (20) to minimize the number of components reducing cost and improve assembly techniques.

In this embodiment the frame members (30, 50) have relative axial positions, with proximal frame member (50) being positioned proximally relative the distal frame member (30). In this embodiment the frame members (30, 50) are ring-shaped and are axially aligned with one another and the passage (21). The ring-shaped frame members (30, 50) define an opening sized to receive a human hand. The frame members (30, 50) can rotate relative one another about a common axis, which in turn adjusts the iris valve (20) between the opened and closed positions. In this embodiment the frame members (30, 50) can rotate relative to one another while maintaining the relative axial positions. In other words, the frame members (30, 50) can rotate without substantial deviation of the relative axial spacing.

The resilient nature of the iris valve may induce a relative rotational bias between the frame members (30, 50) toward the opened position. A lock may be used to prevent the relative rotational movement induced by the iris valve (20) bias. In the present embodiment the frame members (30, 50) can rotate relative to one another in a first rotational direction to open the iris valve (20) only when the lock is released; however, the lock will not prevent the frame members (30, 50) from rotating relative one another in a second rotational direction to close the iris valve (20).

The present embodiment includes a control ring (40) that also has a relative axial position relative the frame members (30, 50). All three components (30, 40, 50) are nested within one another. The control ring (40) is operatively to selectively release the lock when turned in the first rotational direction relative the distal frame member (30). In addition, when turned in the second rotational direction relative the distal frame member (30), the control ring (40) engages the proximal frame member (50) and urges the iris valve (20) toward the closed position. During such use, the control ring (40) and the frame members (30, 50) all maintain their the relative axial positions. Thus, the opening and closing the iris valve (20) may be achieved by simply rotating the control ring (40) in the appropriate direction.

Optionally, the relative rotational movement of the frame members (30, 50) may be constrained to less than 270 degrees. In the present embodiment the control ring (40) includes an arcuate channel spanning about 245 degrees. A nub extends from the distal frame member (30) and rides in the channel. The two ends of the channel operate as stops against the nub limiting the rotational range of movement to within the channel, thus limiting the relative rotational movement between the control ring (40) and distal frame member (30). Since the rotational position of the proximal frame member (50) is dependent on the position of the control ring (40), the channel and nub cooperate to limit the relative rotational movement of the frame members (30, 50) to about 245 degrees.

FIGS. 4-7 illustrate internal features the access device (10). The lock comprises a ratchet (33) and pawl (55) mechanism. The ratchet (33) is attached to the distal frame member (30). Optionally, the ratchet (33) may have an arcuate span less than 270 degrees. The ratchet (33) comprises teeth that are radially oriented and face laterally outward, but other teeth arrangements are also contemplated including axial or medial facing teeth. The pawl (55) pivots about the pin (56) that is attached to the proximal frame member (50). A biasing member (57), shown in this embodiment as a spring, biases the pawl (55) to engage the ratchet (33). A pusher (41) is attached to the control ring (40). As the control ring (40) is rotated in the closing direction, the position of the pusher (41) will move between the pawl (55) and the stop (53) on the proximal frame member (50). The pusher (41) has an angular stroke of between less than about 30 degrees between the pawl (55) and the stop (53). The control ring (40) has three operating positions or states, depending on the position of the pusher (41) within its angular stroke.

Figure 5:
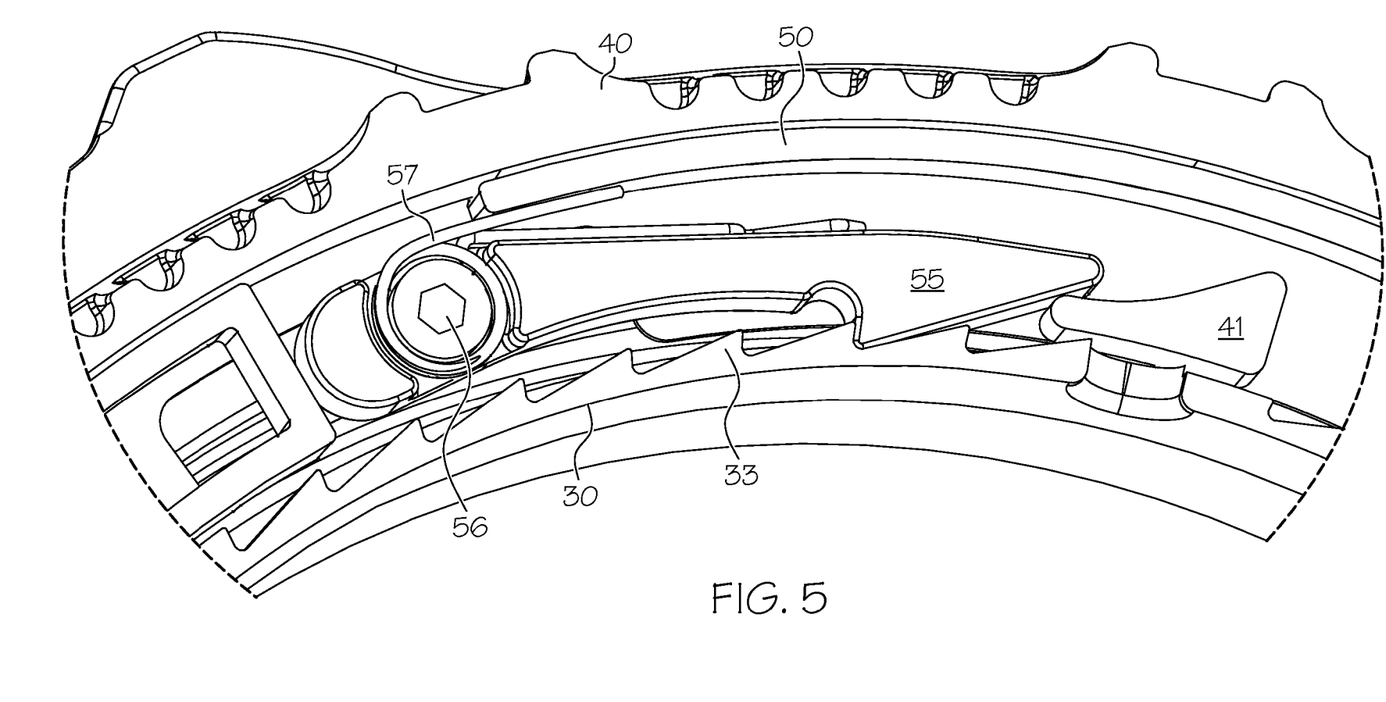
FIG. 5 depicts a cross-section of a lock mechanism in a neutral position.

In the neutral position or state, as demonstrated in FIG. 5, the pusher (41) is positioned anywhere within its angular stroke without operatively engaging the pawl (55) or the stop (53). The pawl (55) is engaged with the ratchet (33) to prevent the rotational bias induced by the iris valve (20) towards the opened position, thus locking the iris valve (20) in its current position. In the neutral state it is contemplated that the control ring (40) may have an idle "play" corresponding to the angular stroke of the pusher (41). Optionally, a spring could be added to bias the pusher (41) against the stop (53).

Figure 6:
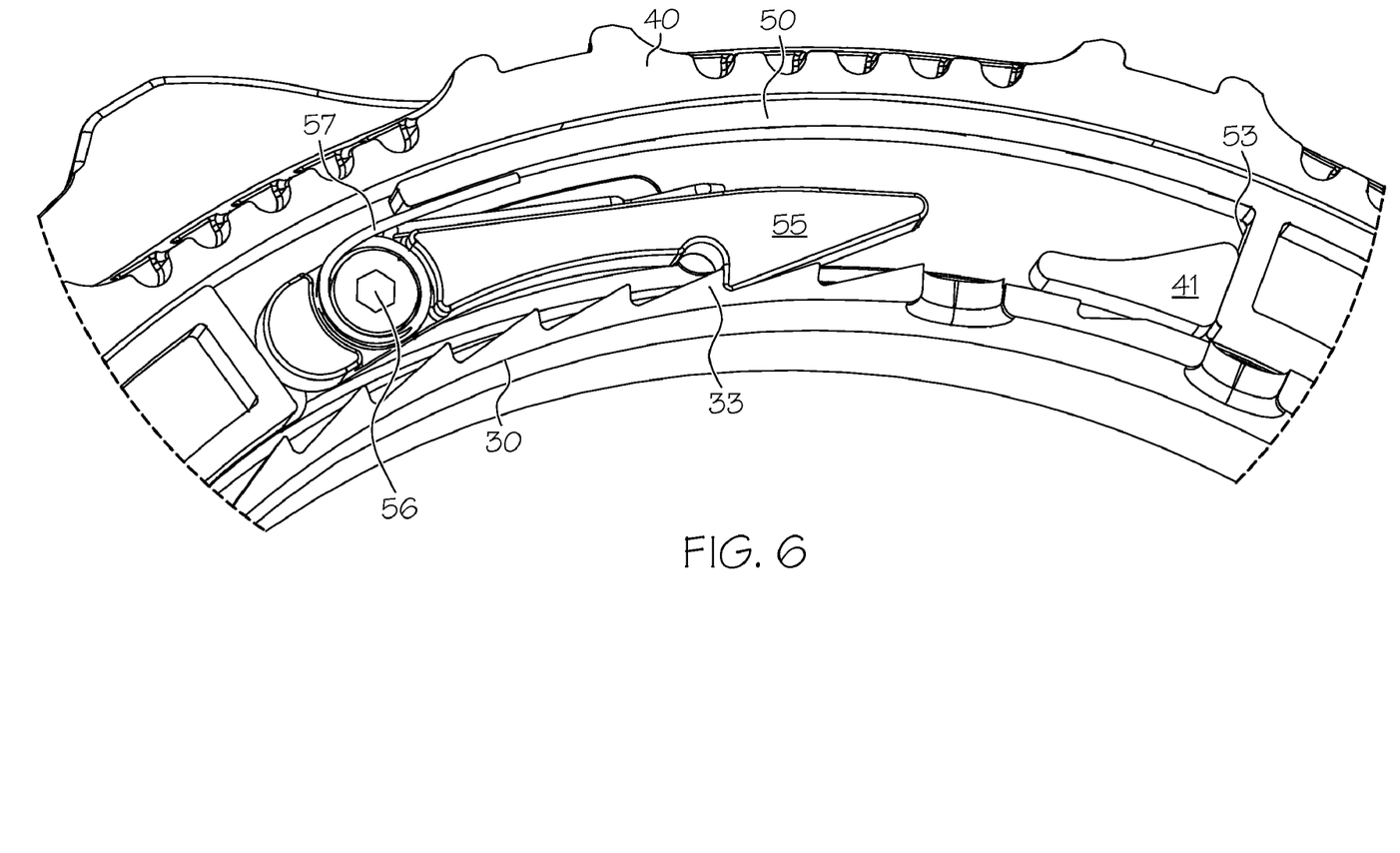
FIG. 6 depicts a cross-section of a lock mechanism in a tightening position.

In the tightening position or state, as demonstrated in FIG. 6, the pusher (41) operatively engages the stop (53) to induced a torque on the proximal frame member (50). When the torque exceeds the bias induced by the iris valve (20), the proximal ring (50) will rotate relative the distal ring (30) and move the iris valve (20) toward the closed position. After sufficient angular movement, the pawl (55) will advance clockwise to the adjacent tooth in the ratchet (33). Accordingly, the iris valve (20) is incrementally closed. Thus, by rotating the control ring (40) clockwise the iris valve (20) will close.

Figure 7:
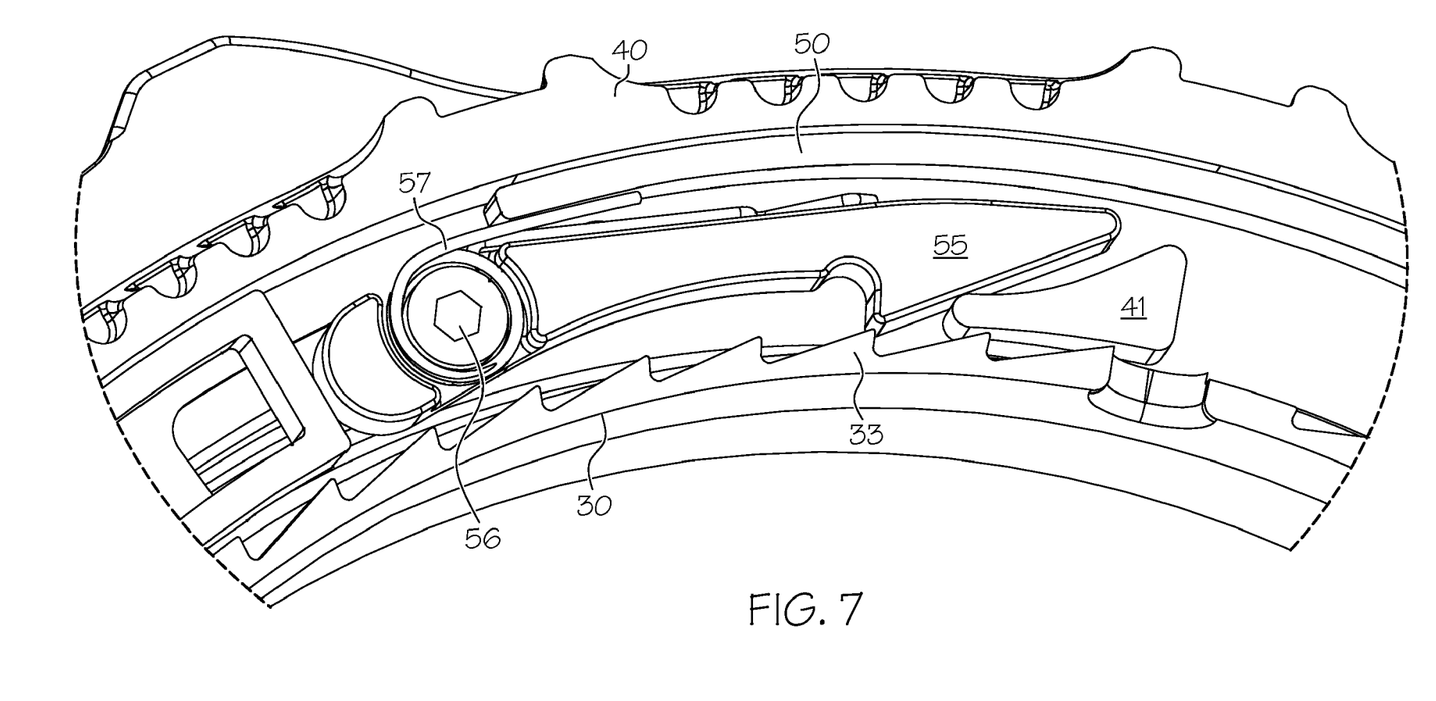
FIG. 7 depicts a cross-section of a lock mechanism in a loosening position.

In the loosening position or state, as illustrated in FIG. 7, the pusher (41) operatively engages the pawl (55) to lift the pawl (55) away from the ratchet (33) and disengage the pawl (5) from the ratchet (33) tooth. The rotational bias induced by the iris valve (20) will act on the proximal frame member (50) and advance the pawl (55) counterclockwise away from the pusher (41). After the pusher (41) disengages the pawl (55), the spring (57) will bias the pawl (55) to reengage the ratchet (33) at the next tooth. Accordingly, the iris valve (20) is incrementally opened. Thus, by rotating the control ring (40) counterclockwise the iris valve (20) will open.

Figure 8:
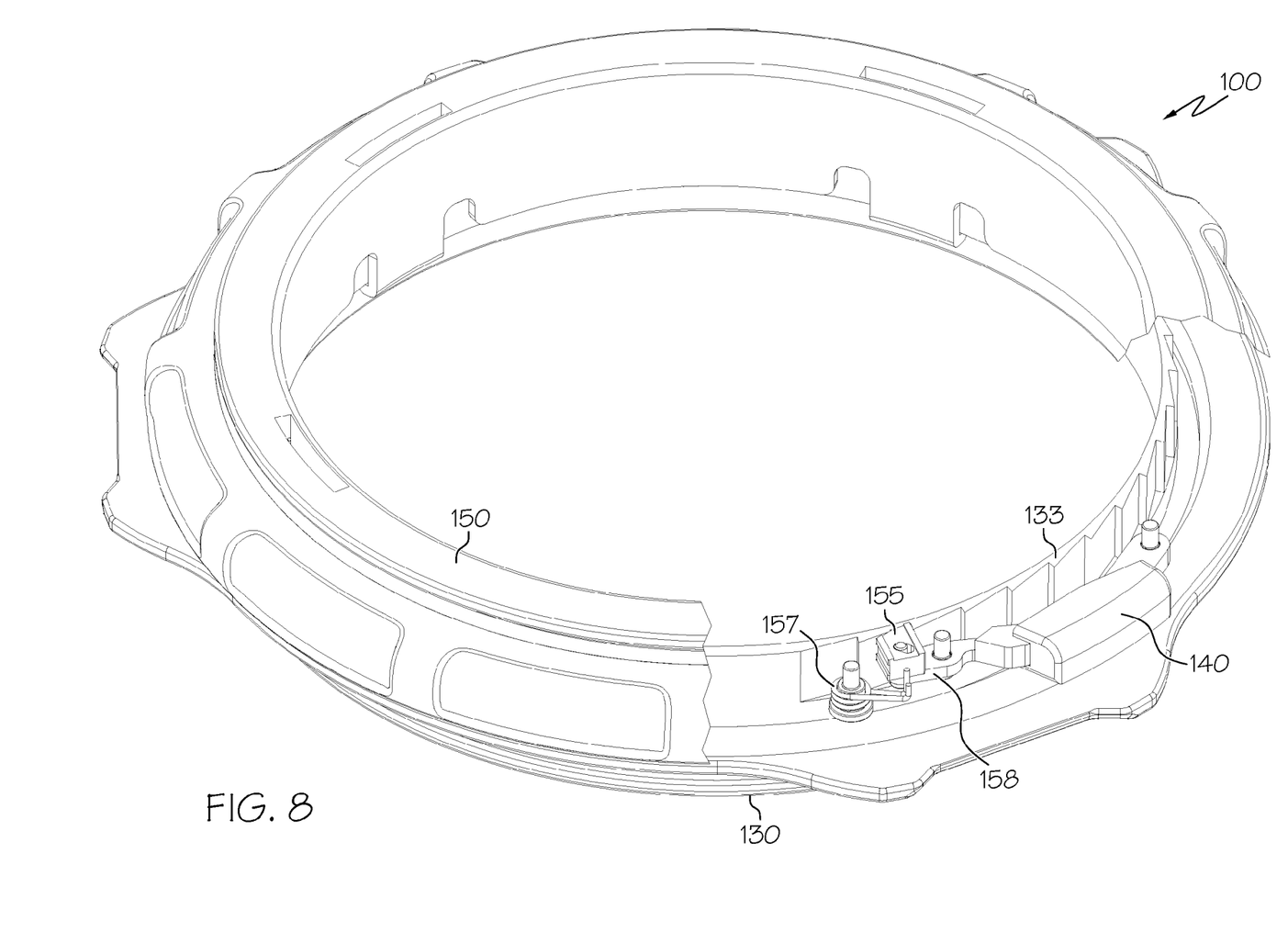
FIG. 8 depicts a perspective view of an access device with partially broken section revealing a lock mechanism.

FIG. 8 illustrates another embodiment of an access device (100) having a ring-shaped proximal frame member (150) and a ring-shaped distal frame member (130) nested within one another. An iris valve (not shown) would be connected to frame members (130, 150) in a similar manner as the frame members (30, 50) and would be operationally and structurally similar to iris valve (20). The frame members (130, 150) can rotate relative one another while maintaining the relative axial positions to open and close the iris valve. A ratchet (133) and pawl (155) lock mechanism is used to prevent relative rotational movement between the frame members (130, 150). In the present embodiment the frame members (130, 150) can rotate relative one another in the first rotational direction to open the iris valve only when the lock is released; however, the lock will not prevent the frame members (130, 150) from rotating relative one another in a second rotational direction to close the iris valve.

The ratchet (133) is attached to the distal frame member (130) and has laterally facing teeth. A spring (157) biases the pawl (155) to engage the ratchet (133). When the pawl (155) is engaged with the ratchet (133), relative rotational movement between the frame members (130, 150) in the first rotational direction is prevented. The lock can be released by depressing the actuator button (140), which it acts on the arm (158) to lift the pawl (155) away from the ratchet (133). Thus, by depressing the button (140) the pawl (155) is disengaged and the proximal frame member (150) may be rotated counterclockwise to open the iris valve. Relative rotational movement between the frame members (130, 150) in the second rotational direction will cause the pawl (155) to advance clockwise to the adjacent tooth in the ratchet (133). Accordingly, the iris valve is incrementally closed. Thus, clockwise rotation of the proximal frame member (150) will close the iris valve.

Figure 9:
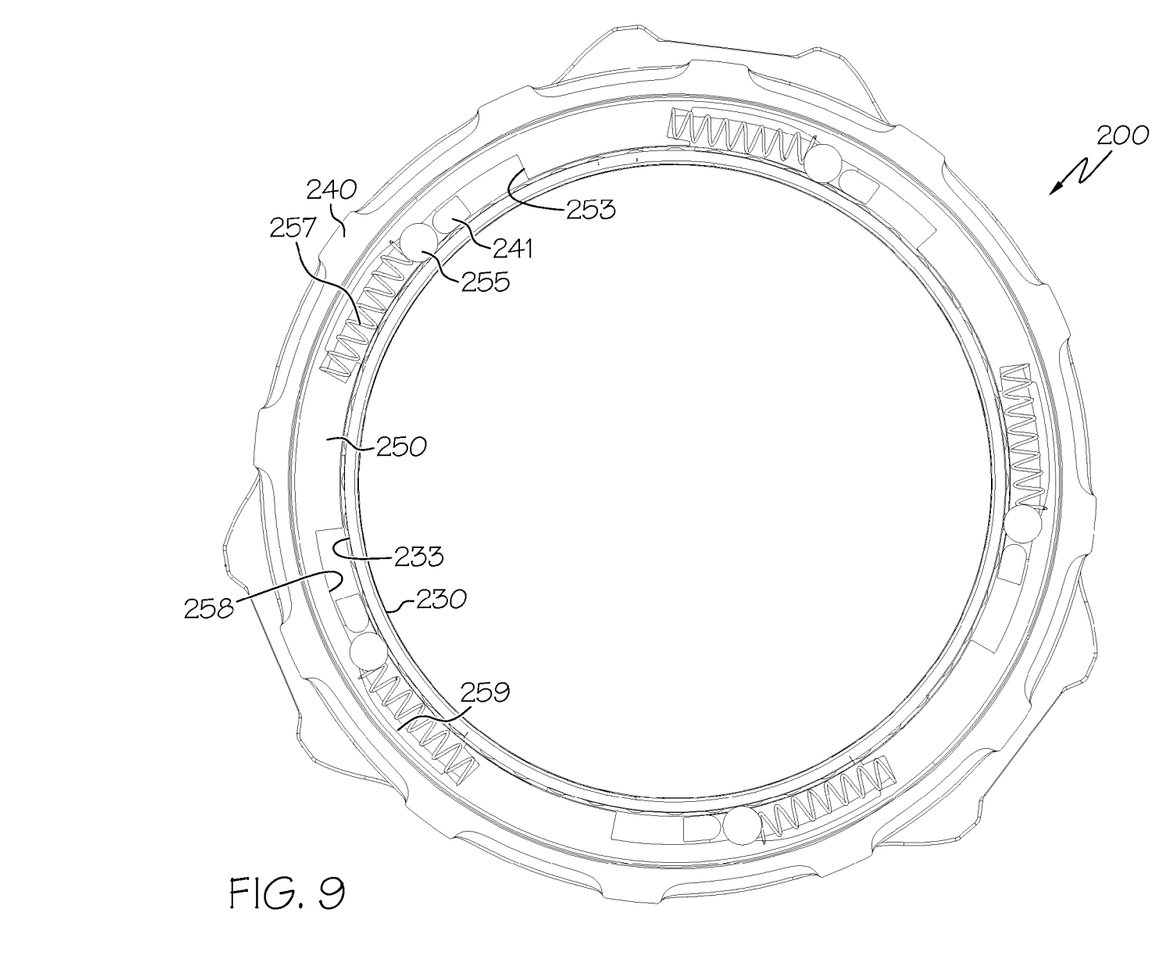
FIG. 9 depicts a cross-section of an access device with a lock mechanism in a neutral position.
Figure 10:
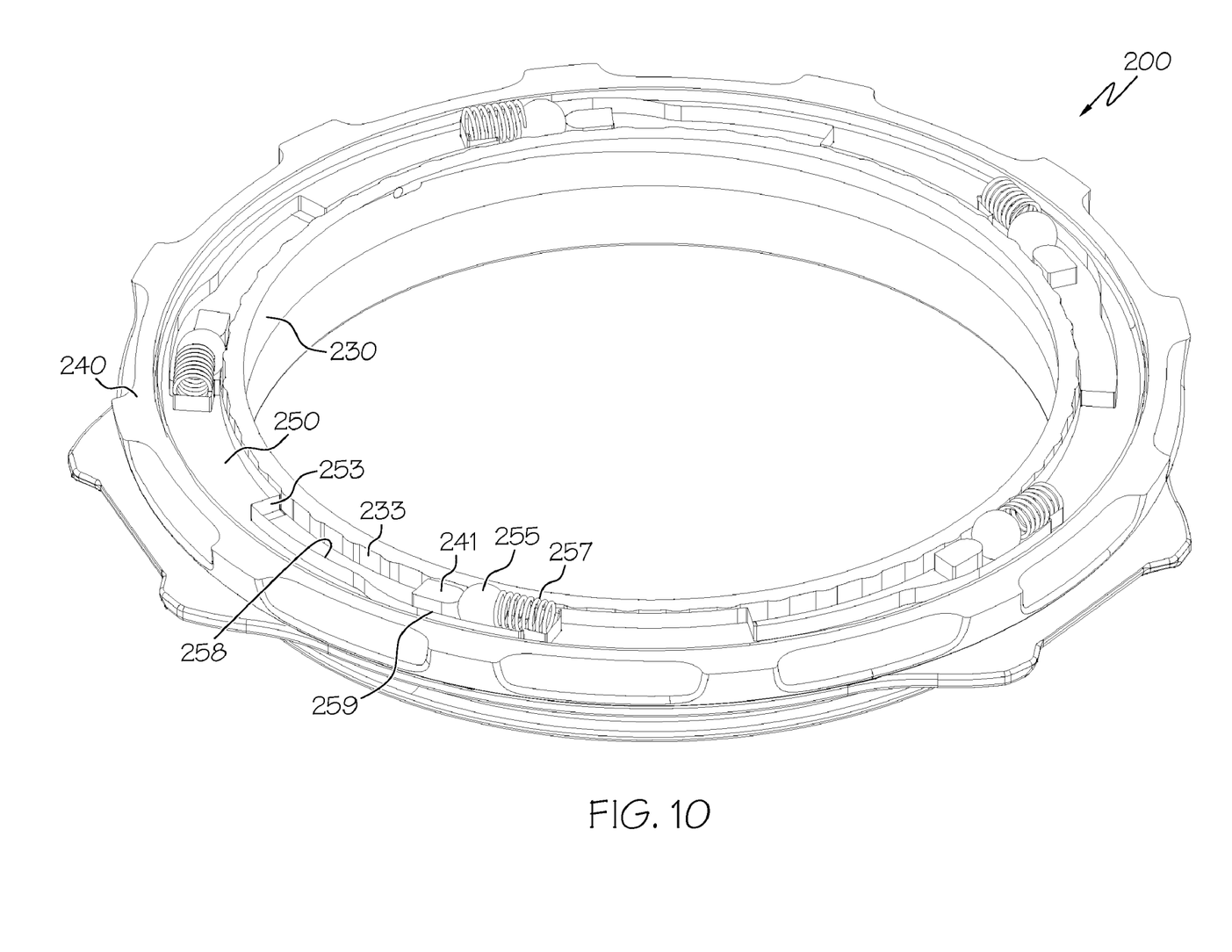
FIG. 10 depicts a perspective cross-section of an access device with a lock mechanism in a loosening position.
Figure 11:
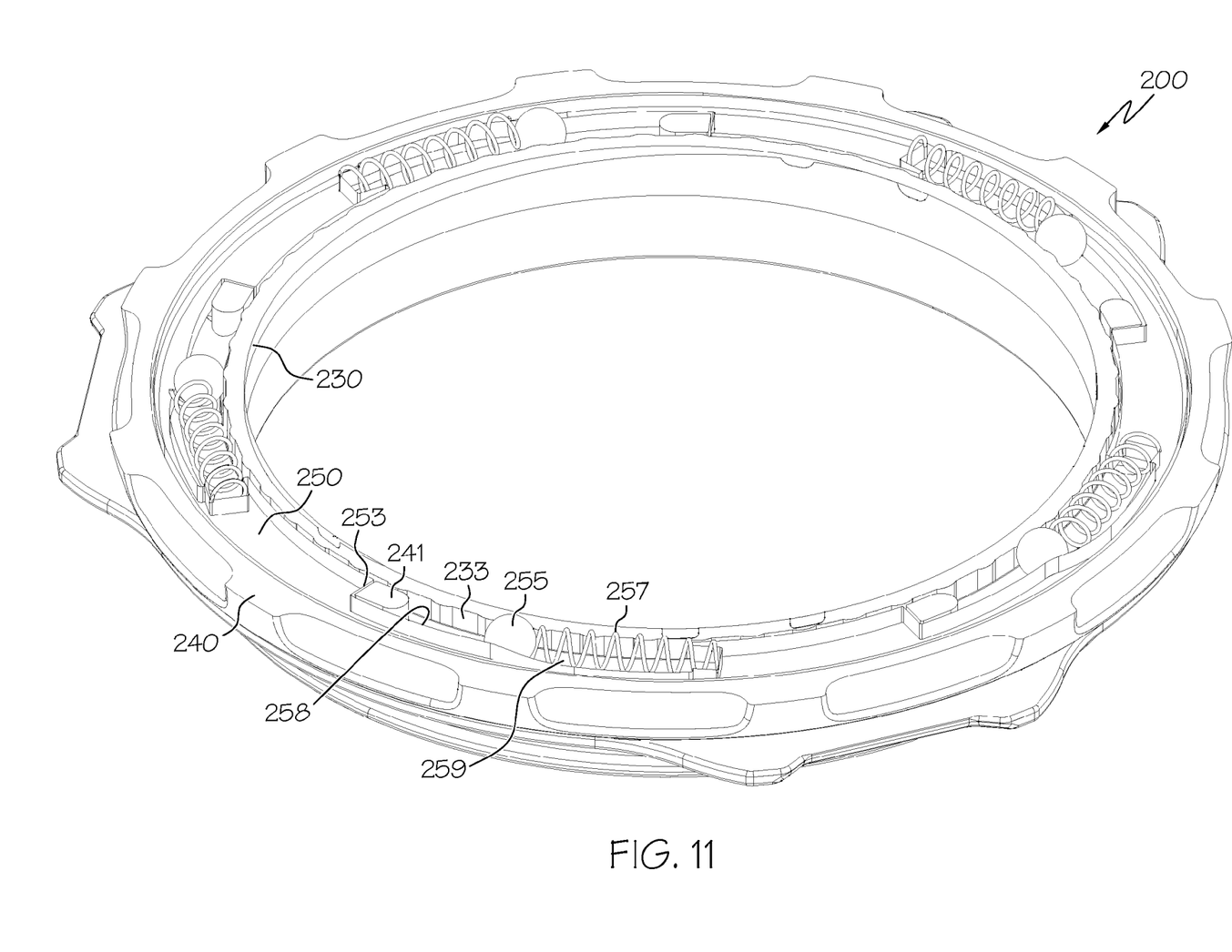
FIG. 11 depicts a perspective cross-section of an access device with a lock mechanism in a tightening position.

FIGS. 9-11 illustrate another embodiment of an access device (200) having a ring-shaped proximal frame member (250), a ring-shaped distal frame member (230), and a control ring (240) nested within one another. An iris valve (not shown) would be connected to frame members (230, 250) in a similar manner as the frame members (30, 50) and would be operationally and structurally similar to iris valve (20). The frame members (230, 250) can rotate relative one another while maintaining the relative axial positions to open and close the iris valve. A lock mechanism is used to prevent relative rotational movement between the frame members (230, 250). In the present embodiment the frame members (230, 250) can rotate relative one another in a first rotational direction to open the iris valve only when the lock is released; however, the lock will not prevent the frame members (230, 250) from rotating relative one another in a second rotational direction to close the iris valve.

Preferably the lock mechanism comprises three or more ball and wedge track mechanisms; however, this embodiment has five ball and wedge track mechanisms. A wall (233) is attached to the distal frame member (230). In this example the wall (233) is textured with axial ribs, but other surfaces could also be used. A track is defined between the wall (233) and the proximal frame member (250). Each track includes a narrow portion (258) that transitions to a wide portion (259). A ball (255) is positioned in the wide portion (259), but the ball (255) is too small to fit in the narrow portion (258). A spring (257) biases the ball (255) toward the narrow portion (258). A pusher (241) is attached to the control ring (240) and is positioned in the narrow portion (258) of the track. As the control ring (240) is rotated, the position of the pusher (241) will move between the ball (255) and the stop (253) on the proximal frame member (250). The pusher (241) has an angular stroke of less than about 30 degrees between the ball (255) and the stop (253). The control ring (240) has three operating positions or states, depending on the position of the pusher (241) within its angular stroke.

In the neutral position or state, as demonstrated in FIG. 9, the pusher (241) is positioned anywhere within its angular stroke without operatively engaging the ball (255) or the stop (253). The balls (255) are wedged in the track where the narrow portion (258) transitions to the wide portion (259). The wedged balls (255) engage both frame members (230, 250) and prevent relative rotational movement in the first rotational direction to open the iris valve. Thus, the wedged balls (255) resist the rotational bias induced by the iris valve and lock the iris valve in its current position. In the neutral state it is contemplated that the control ring (240) may have an idle "play" corresponding to the angular stroke of the pusher (241).

In the loosening position or state, as illustrated in FIG. 10, the pusher (241) operatively engages the ball (255) pushing it toward the wide portion (259) thus liberating the ball (255) from being wedged in the track. The rotational bias induced by the iris valve will act on the proximal frame member (250) and advance the proximal frame member (250) counterclockwise disengaging the pusher (241) from the ball (255). The spring (257) will then bias the ball (255) back into its wedged position. Accordingly, the iris valve is incrementally opened. Thus, by rotating the control ring (240) counterclockwise the iris valve will open.

In the tightening position or state, as demonstrated in FIG. 11, the pusher (241) operatively engages the stop (253) to induced a torque on the proximal frame member (250). When the torque exceeds the rotational bias induced by the iris valve, the proximal ring (250) will rotate relative the distal ring (230) and move the iris valve toward the closed position. Due to the direction of the track transition between the narrow and wide portions (258, 259), the ball (255) will not prevent relative rotational movement in the second rotational direction to close the iris valve. Accordingly, the iris valve is incrementally closed. Thus, by rotating the control ring (240) clockwise the iris valve will close.

Preferably, the access devices described above will be processed before surgery. First, a new or used access device is obtained and if necessary cleaned. The access device can then be sterilized. In one sterilization technique the access device is placed in a closed and sealed container, such as a plastic or TYVEK bag. Optionally, the access device can be bundled in the container as a kit with other components, including one or more of the following: a wound protector, a mounting ring for the wound protector, a tube of lubricant, a marker, an incision template or scale, an instruction sheet, and the like. The container and access device, as well as any other components, are then placed in a field of radiation that can penetrate the container, such as gamma radiation, x-rays, or high-energy electrons. The radiation kills bacteria on the access device and in the container. The sterilized access device can then be stored in the sterile container. The sealed container keeps the access device sterile until it is opened in the medical facility.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. In addition, the foregoing teachings could be implemented for non-HALS procedures, such as reducing the scale to seal against instruments in traditional laparoscopic procedures. Accordingly, the scope of the present invention should be considered in terms of the following claims and is understood not to be limited to the details of structure, materials, or acts shown and described in the specification and drawings.

The invention claimed is:

1. A surgical access port for the hand, comprising:
   a) a first ring and a second ring rotateable relative one another about a common axis, the first and second rings defining an opening sized to receive a human hand;
   b) a flexible and resilient iris valve positioned in the opening and connected to the first and second rings, the iris valve having a closed position and an opened position depending on the relative angular position of the first and second rings, the iris valve inducing a rotational bias between the first and second rings towards the opened position;
   c) a lock connected to the first and second rings preventing relative rotational movement towards the opened position;
   d) a third ring rotateable relative the first and second rings, the third ring being operable to release the lock and open the iris valve when rotated in a first rotational direction whereby the third ring maintains an axial position relative to the first ring and second ring during rotation.

2. The surgical access port of claim 1, wherein the lock comprises a ratchet and pawl.

3. The surgical access port of claim 2, wherein the third ring comprises a pawl lifter that disengages the pawl from the ratchet when rotated in the first rotational direction.

4. The surgical access port of claim 1, wherein the lock comprises a ball interposed between the first and second rings, the ball having a locked position where the ball engages both rings to prevent relative rotational movement towards the opened position and an unlocked position.

5. The surgical access port of claim 4, wherein the third ring comprises pusher operable to move the ball from the locked to unlocked positions when rotated in the first rotational direction.

6. The surgical access port of claim 1, wherein the first ring is proximal the second ring.

7. The surgical access port of claim 1, wherein the first, second, and third rings are nested within one another.

8. A surgical access port, comprising:
   a) a first ring and a second ring defining an opening, the first ring being rotateable relative the second ring in an opening direction and being rotateable relative the second ring in a closing direction;
   b) a flexible and resilient iris valve positioned in the opening and connected to the first and second rings, the iris valve having a closed position and an opened position based on the relative angular position of the first and second rings, the iris valve inducing a rotational bias on the first ring in the opening direction;
c) a lock connected to the first and second rings counteracting the iris valve rotational bias;
d) a third ring operable to release the lock when rotated in the opening direction and being operable to close the valve when rotated in the closing direction.

9. The surgical access port of claim 8, wherein the first ring is proximal the second ring.

10. A sterile surgical kit, comprising the surgical access port of claim 8 and a wound protector.

11. A surgical access device, comprising:
a) a proximal ring;
b) a distal ring;
c) an iris valve connected to the proximal and distal ring, the iris valve having a closed position and an opened position based on the relative angular position of the proximal and distal rings;
d) a control ring rotateable relative the proximal and distal rings, the control ring comprising:
(i) a neutral state wherein the iris valve is locked in its current position;
(ii) a loosening state wherein rotational movement of the control ring in a first direction will adjust the iris valve toward the opened position; and
(iii) a tightening state wherein rotational movement of the control ring in a second direction will adjust the iris valve toward the closed position.

12. The surgical access device of claim 11, further comprising a lock preventing relative rotational movement between the proximal and distal rings.

13. The surgical access device of claim 12, wherein in loosening state the control ring disengages the lock.

14. The surgical access device of claim 12, wherein the lock comprises a ratchet and pawl.

15. The surgical access device of claim 11, wherein in the neutral state the control ring has a angular stroke of less than about 30 degrees.

16. The surgical access device of claim 11, wherein in tightening state the control ring engages the proximal ring to urge relative rotational movement relative the distal ring.

17. A sterile surgical kit, comprising the surgical access device of claim 11 and a wound protector.

* * * * *